(12) United States Patent
Braun et al.

(10) Patent No.: US 11,122,356 B1
(45) Date of Patent: Sep. 14, 2021

(54) ANIMAL HEADPHONE ASSEMBLY

(71) Applicants: Angela Braun, Bothell, WA (US); David Castro, Bothell, WA (US)

(72) Inventors: Angela Braun, Bothell, WA (US); David Castro, Bothell, WA (US)

( * ) Notice: Subject to any disclaimer, the term of this patent is extended or adjusted under 35 U.S.C. 154(b) by 0 days.

(21) Appl. No.: 16/855,595

(22) Filed: Apr. 22, 2020

(51) Int. Cl.
*H04R 1/10* (2006.01)
*A01K 13/00* (2006.01)

(52) U.S. Cl.
CPC .......... *H04R 1/105* (2013.01); *A01K 13/006* (2013.01); *H04R 1/1066* (2013.01)

(58) Field of Classification Search
CPC .. H04R 1/105; H04R 1/1041; H04R 2460/07; H04R 5/02; H04R 1/1016; H04R 1/403
See application file for complete search history.

(56) References Cited

U.S. PATENT DOCUMENTS

| | | | |
|---|---|---|---|
| 3,942,306 A | 3/1976 | Kulka | |
| 5,163,272 A | 11/1992 | Finley | |
| 6,591,786 B1 | 7/2003 | Davis | |
| 7,946,256 B2 | 5/2011 | Mann | |
| D677,437 S | 3/2013 | Dunston | |
| 9,628,895 B2 | 4/2017 | Malaviya | |
| 2007/0062462 A1* | 3/2007 | McGuire | A01K 13/006 119/850 |
| 2009/0178628 A1 | 7/2009 | Carmean | |
| 2014/0247951 A1* | 9/2014 | Malaviya | H04R 1/105 381/74 |

\* cited by examiner

*Primary Examiner* — Amir H Etesam

(57) ABSTRACT

An animal headphone assembly for soothing a canine when the canine is exposed to distressing sounds includes a pair of headphones. Each of the headphones has a diameter sufficient to cover ears of a canine for wearing over each of a canine's ears. A plurality of straps is each coupled between each of the headphones to extend around the canine's head for retaining the headphones over the canine's ears. A sound unit is integrated into the headphones to emit sound outwardly therefrom. The sound unit stores a database comprising a plurality of musical songs to emit pleasing sounds into the canine's ears. Each of the musical songs includes concealed binaural beats to soothe the canine.

8 Claims, 5 Drawing Sheets

ANIMAL HEADPHONE ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to animal headphone devices and more particularly pertains to a new animal headphone assembly for soothing a canine when the canine is exposed to distressing sounds.

(2) Description of Related Art Including Information Disclosed Under 37 CFR 1.97 and 1.98

The prior art relates to animal headphone devices including an animal noise protection device that includes a box in which an animal can rest and a sound baffle extending into the box for reducing noise that enters the box. The prior art additionally discloses an ear covering scarf that can be worn around an animal's ears. The prior art discloses a wireless communication device that includes an earpiece that goes into an animal's ear and a microphone that is carried by a trainer of the animal. Additionally, the prior art discloses an ear covering device that is worn around an animal's ears that includes flaps that can be positioned over the animal's ears for protecting the animal's ears from loud sounds. The prior art also discloses a pair of earbuds that are wearable in an animal's ears for playing soothing music.

BRIEF SUMMARY OF THE INVENTION

An embodiment of the disclosure meets the needs presented above by generally comprising a pair of headphones. Each of the headphones has a diameter sufficient to cover ears of a canine for wearing over each of a canine's ears. A plurality of straps is each coupled between each of the headphones to extend around the canine's head for retaining the headphones over the canine's ears. A sound unit is integrated into the headphones to emit sound outwardly therefrom. The sound unit stores a database comprising a plurality of musical songs to emit pleasing sounds into the canine's ears. Each of the musical songs includes concealed binaural beats to soothe the canine.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
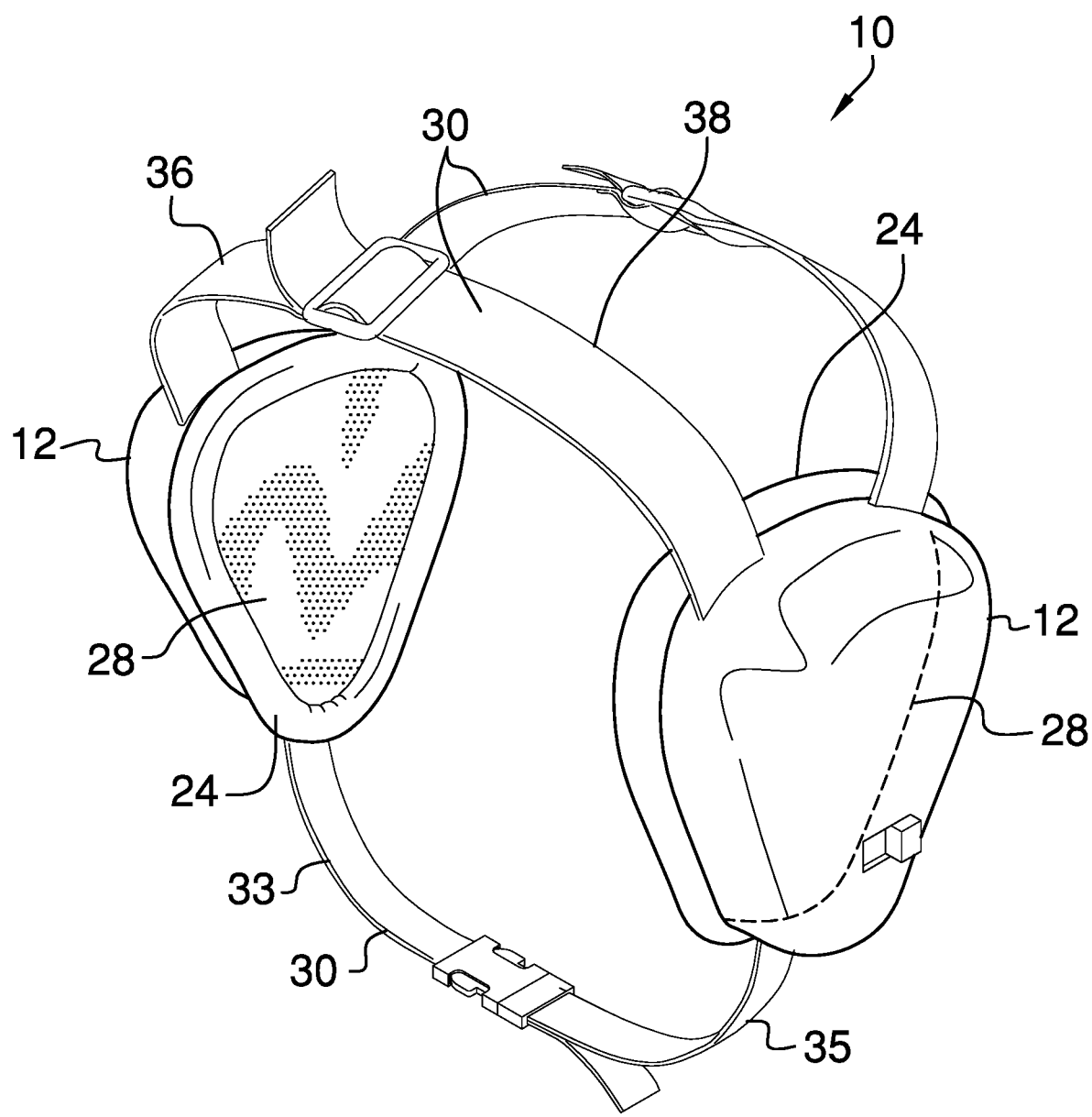
FIG. 1 is a perspective view of an animal headphone assembly according to an embodiment of the disclosure.
Figure 2:
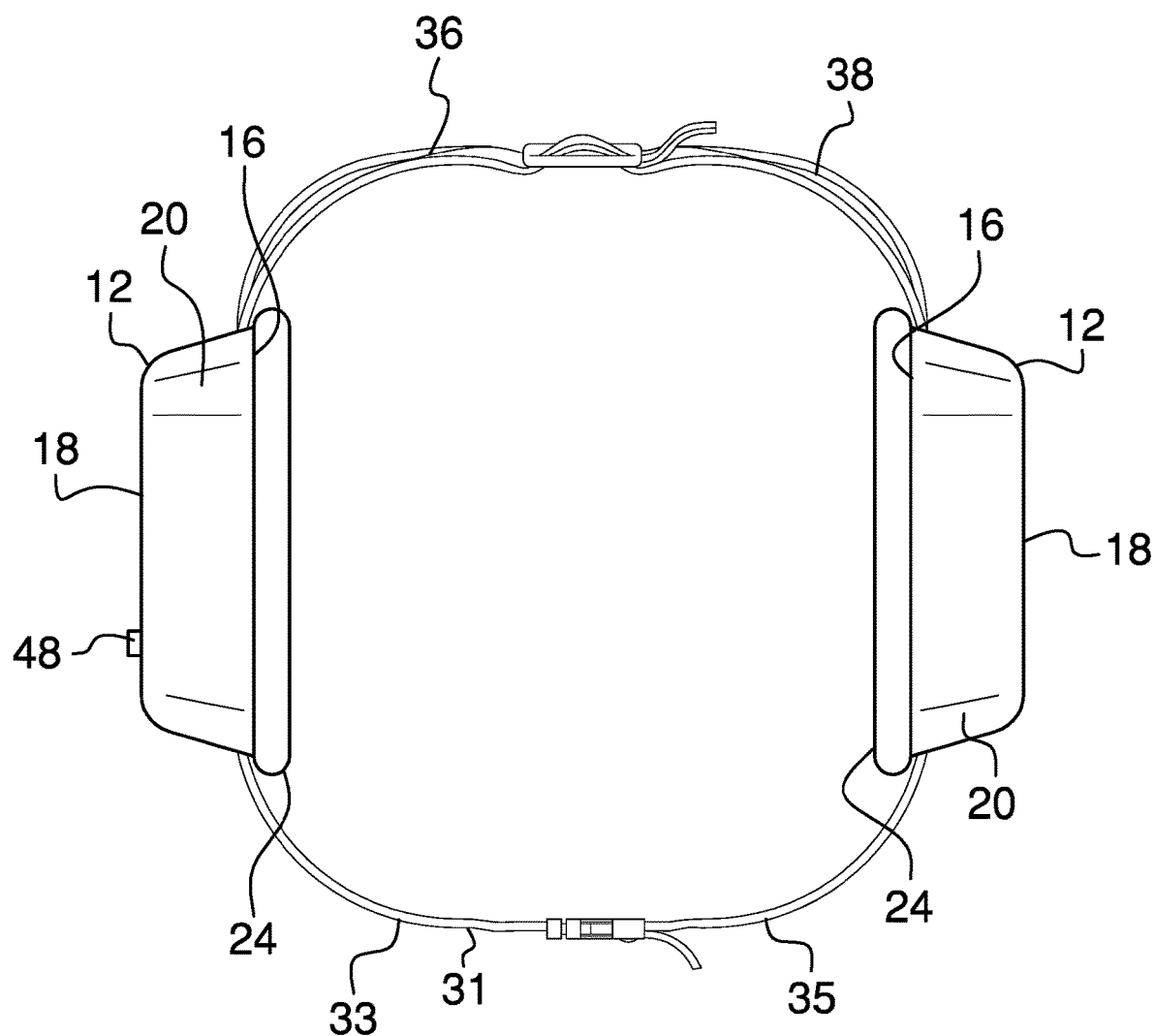
FIG. 2 is a front view of an embodiment of the disclosure.
Figure 3:
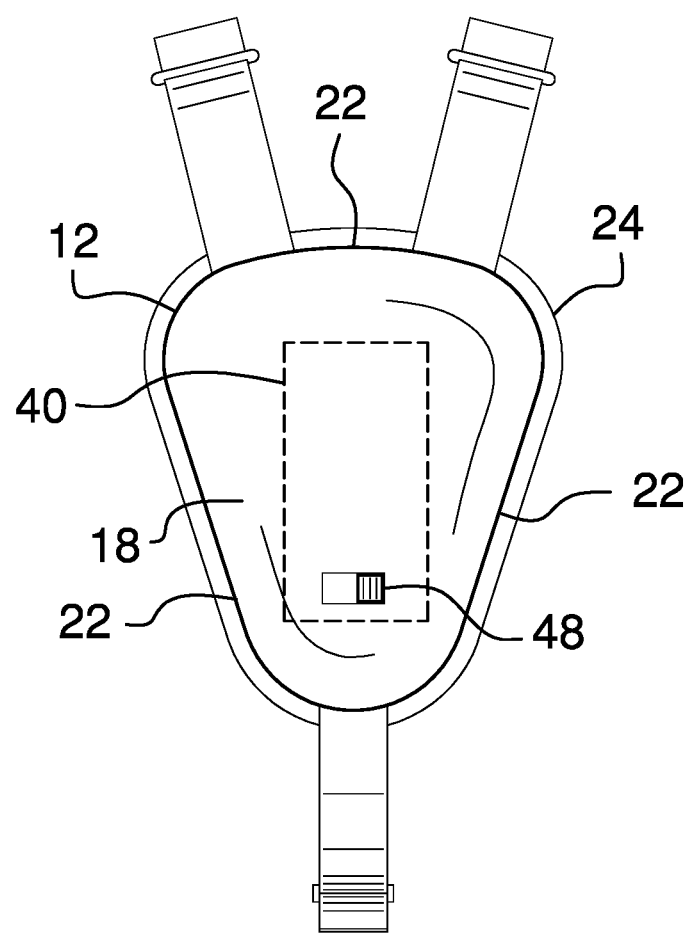
FIG. 3 is a right side view of an embodiment of the disclosure.
Figure 4:
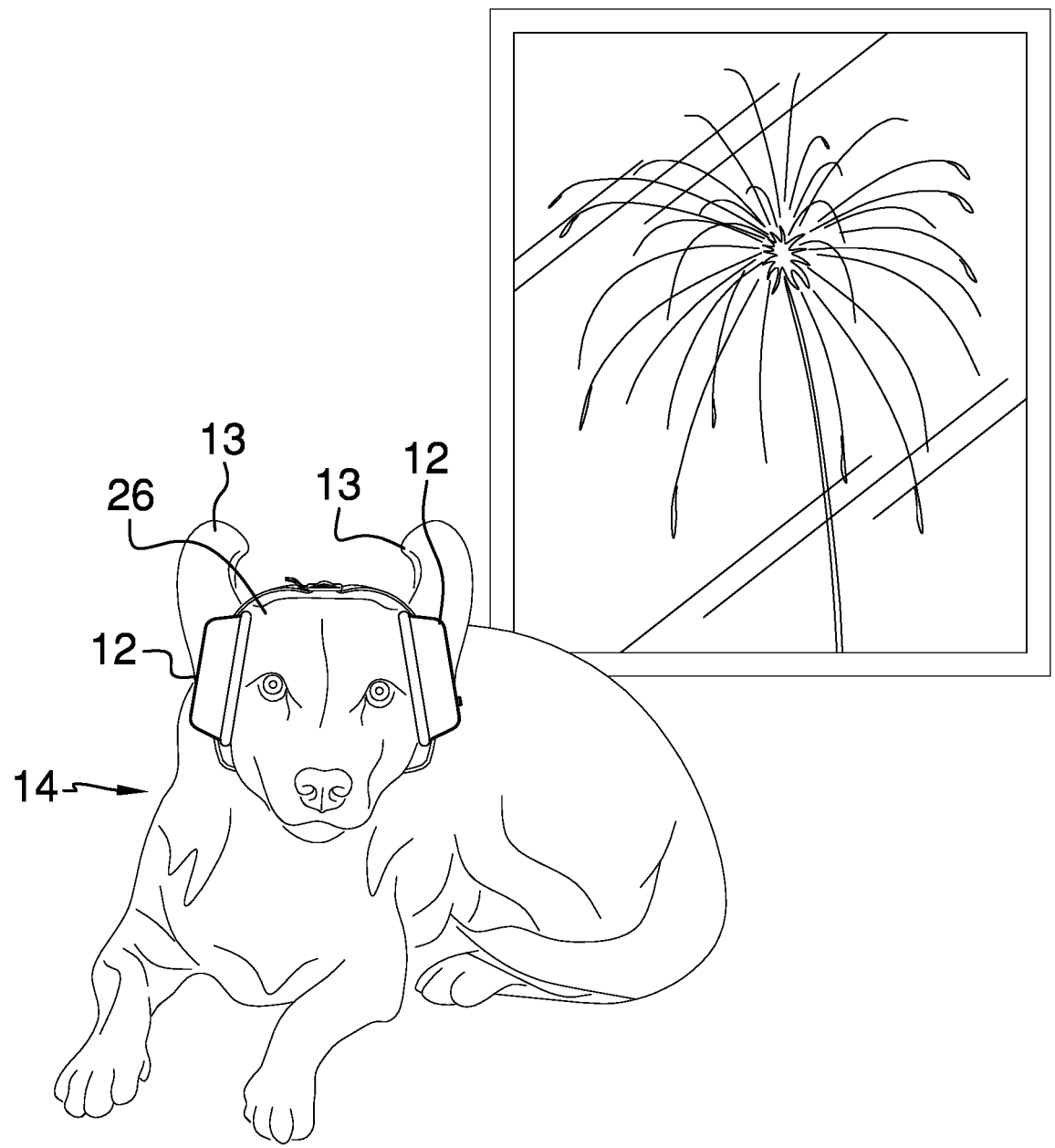
FIG. 4 is a perspective in-use view of an embodiment of the disclosure.
Figure 5:
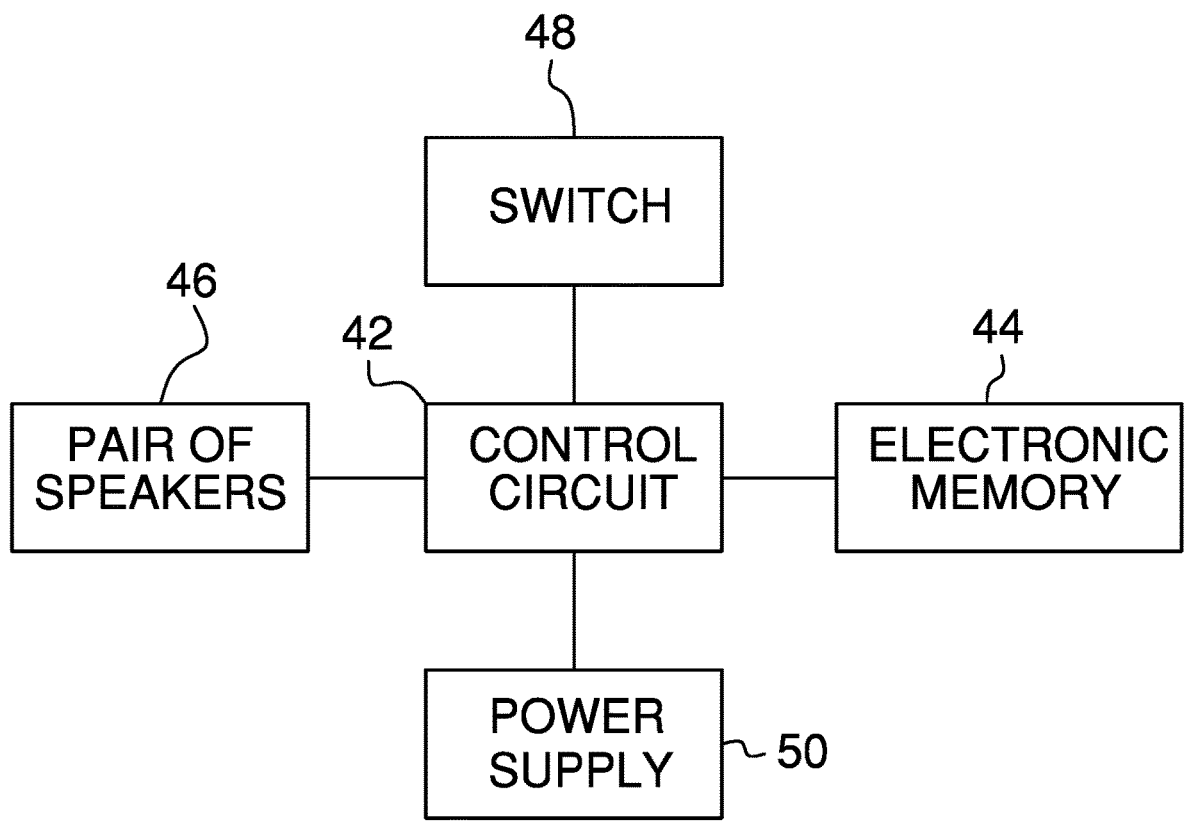
FIG. 5 is a schematic view of an embodiment of the disclosure.

With reference now to the drawings, and in particular to FIGS. 1 through 5 thereof, a new animal headphone assembly embodying the principles and concepts of an embodiment of the disclosure and generally designated by the reference numeral 10 will be described.

As best illustrated in FIGS. 1 through 5, the animal headphone assembly 10 generally comprises a pair of headphones 12. Each of the headphones 12 has a diameter sufficient to cover ears 13 of a canine 14 thereby facilitating each of the headphones 12 to be worn over each of a canine's ears 13. Each of the headphones 12 has a front side 16, a back side 18 and an outer side 20 extending therebetween. The outer side 20 has a plurality of intersecting sides 22 such that each of the headphones 12 has a triangular shape for accommodating ears of the canine 14, and the front side 16 is open into an interior of the headphones 12. Each of the headphones 12 may be comprised of a sound resistant material such as plastic or the like.

A pair of cushions 24 is each coupled to the front side 16 of a respective one of the headphones 12 to abut the canine's head 26 when the headphones 12 are worn on the canine's head 26. Each of the cushions 24 is positioned on the front side 16 of the respective headphone 12. Additionally, each of the cushions 24 is coextensive with an intersection between the front side 16 and the outer side 20 of the respective headphone 12. A pair of membranes 28 is provided and each of the membranes 28 is coupled to a respective one of the headphones 12. Each of the membranes 28 is comprised of a sound permeable material to pass sound therethrough.

Each of the membranes 28 is positioned on the front side 16 of the respective headphone 12 such that each of the membranes 28 covers the front side 16.

A plurality of straps 30 is provided and each of the straps 30 is coupled between each of the headphones 12. Each of the straps 30 extends around the canine's head 26 for retaining the headphones 12 over the canine's ears 13. Each of the straps 30 has a first end 32 and a second end 34, and the first end 32 of each of the straps 30 is coupled to a respective one of the intersecting sides 22 of the outer side 20 of a respective one of the headphones 12. The second end 34 of each of the straps 30 is coupled to a respective one of the intersecting sides 22 of the outer side 20 of a respective one of the headphones 12. Each of the straps 30 comprises a first portion 36 that slidably engages a second portion 38 such that each of the straps 30 has an adjustable length. The straps 30 may include a chin strap 31 that is divided into a first half 33 and a second half 35, and the first half 33 may be matable or unmatable to the second half 35.

A sound unit 40 is integrated into the headphones 12 to emit sound outwardly therefrom. The sound unit 40 stores a database comprising a plurality of musical songs to emit pleasing sounds into the canine's ears 13. Moreover, each of the musical songs includes concealed binaural beats to soothe the canine 14. In this way the canine 14 can be comforted when fireworks are being exploded, when thunder is occurring or during any other occasion that involves sounds that are distressing to the canine 14.

The sound unit 40 comprises a control circuit 42 that is integrated into the headphones 12 and an electronic memory 44 is integrated into the headphones 12. The electronic memory 44 is electrically coupled to the control circuit 42 and the electronic memory 44 stores the database comprising the plurality of musical songs and the concealed binaural beats. The sound unit 40 includes a pair of speakers 46 and each of the speakers 46 is coupled to a respective one of the headphones 12 to emit audible sound outwardly therefrom. Each of the speakers 46 is directed toward the membrane 28 on the respective headphone 12 to direct the audible sound into the canine's ears 13 when the headphones 12 are worn. The control circuit 42 may include a solid state amplifier and other components common to audio equipment.

The sound unit 40 includes a switch 48 is slidably coupled to a respective one of the headphones 12. The switch 48 is electrically coupled to the control circuit 42 and the switch 48 is positionable between an on position and an off position for turning the control circuit 42 on and off. The sound unit 40 includes a power supply 50 that is integrated into a respective one of the headphones 12. The power supply 50 is electrically coupled to the control circuit 42 and the power supply 50 comprises at least one rechargeable battery.

In use, the headphones 12 are worn on the canine's head 26 and each of the straps 30 is adjusted to tighten the headphones 12 on the canine's head 26. The headphones 12 are worn on the canine's head 26 when the canine 14 is exposed to distressing sounds, including but not being limited to, the sound of exploding fireworks or thunder. The switch 48 is positioned in the on position to turn on the control circuit 42 and to emit the audible sounds from the speakers 46. In this way the canine 14 is soothed with the musical songs along with the concealed binaural beats. Thus, the headphones 12 reduce the stress response in the canine 14 with respect to the distressing sounds.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. An animal headphone assembly for emitting soothing sounds into an animal's ears, said assembly comprising:
 a pair of headphones, each of said headphones having a diameter sufficient to cover ears of a canine wherein each of said headphones is configured to be worn over each of a canine's ears;
 a plurality of straps, each of said straps being coupled between each of said headphones wherein each of said straps is configured to extend around the canine's head for retaining said headphones over the canine's ears;
 a sound unit being integrated into said headphones wherein said sound unit is configured to emit sound outwardly therefrom, said sound unit storing a database comprising a plurality of musical songs wherein said sound unit is configured to emit pleasing sounds into the canine's ears, each of said musical songs including concealed binaural beats wherein said sound unit is configured to soothe the canine; and
 wherein said sound unit comprises
  a control circuit being integrated into said headphones,
  an electronic memory being integrated into said headphones, said electronic memory being electrically coupled to said control circuit, said electronic memory storing said database comprising said plurality of musical songs and said concealed binaural beats, and
  a pair of speakers, each of said speakers being coupled to a respective one of said headphones wherein each of said speakers is configured to emit audible sound outwardly therefrom, each of said speakers being directed toward a membrane on said respective headphone wherein each of said speakers is configured to direct the audible sound into the canine's ears when said headphones are worn.

2. The assembly according to claim 1, wherein each of said headphones has a front side, a back side and an outer side extending therebetween, said outer side having a plurality of intersecting sides such that each of said headphones has a triangular shape for accommodating ears of the canine, said front side being open into an interior of said headphones.

3. The assembly according to claim 2, further comprising a pair of cushions, each of said cushions being coupled to said front side of a respective one of said headphones wherein each of said cushions is configured to abut the canine's head when said headphones are worn on the canine's head, each of said cushions being positioned on said front side of said respective headphone, each of said cushions being coextensive with an intersection between said front side and said outer side of said respective headphone.

4. The assembly according to claim 2, further comprising a pair of membranes, each of said membranes being coupled to a respective one of said headphones, each of said membranes being comprised of a sound permeable material wherein each of said membranes is configured to pass sound therethrough, each of said membranes being positioned on said front side of said respective headphone such that each of said membranes covers said front side.

5. The assembly according to claim 2, wherein each of said straps has a first end and a second end, said first end of each of said straps being coupled to a respective one of said intersecting sides of said outer side of a respective one of said headphones, said second end of each of said straps being coupled to a respective one of said intersecting sides of said outer side of a respective one of said headphones, each of said straps comprising a first portion slidably engaging a second portion such that each of said straps has an adjustable length.

6. An animal headphone assembly for emitting soothing sounds into an animal's ears, said assembly comprising:
- a pair of headphones, each of said headphones having a diameter sufficient to cover ears of a canine wherein each of said headphones is configured to be worn over each of a canine's ears;
- a plurality of straps, each of said straps being coupled between each of said headphones wherein each of said straps is configured to extend around the canine's head for retaining said headphones over the canine's ears;
- a sound unit being integrated into said headphones wherein said sound unit is configured to emit sound outwardly therefrom, said sound unit storing a database comprising a plurality of musical songs wherein said sound unit is configured to emit pleasing sounds into the canine's ears, each of said musical songs including concealed binaural beats wherein said sound unit is configured to soothe the canine; and
- wherein said sound unit comprises:
  - a control circuit being integrated into said headphones,
  - an electronic memory being integrated into said headphones, said electronic memory being electrically coupled to said control circuit, said electronic memory storing said database comprising said plurality of musical songs and said concealed binaural beats, and
  - a switch being slidably coupled to a respective one of said headphones, said switch being electrically coupled to said control circuit, said switch being positionable between an on position and an off position for turning said control circuit on and off.

7. An animal headphone assembly for emitting soothing sounds into an animal's ears, said assembly comprising:
- a pair of headphones, each of said headphones having a diameter sufficient to cover ears of a canine wherein each of said headphones is configured to be worn over each of a canine's ears;
- a plurality of straps, each of said straps being coupled between each of said headphones wherein each of said straps is configured to extend around the canine's head for retaining said headphones over the canine's ears;
- a sound unit being integrated into said headphones wherein said sound unit is configured to emit sound outwardly therefrom, said sound unit storing a database comprising a plurality of musical songs wherein said sound unit is configured to emit pleasing sounds into the canine's ears, each of said musical songs including concealed binaural beats wherein said sound unit is configured to soothe the canine; and
- wherein said sound unit comprises:
  - a control circuit being integrated into said headphones,
  - an electronic memory being integrated into said headphones, said electronic memory being electrically coupled to said control circuit, said electronic memory storing said database comprising said plurality of musical songs and said concealed binaural beats, and
  - a power supply being integrated into a respective one of said headphones, said power supply being electrically coupled to said control circuit, said power supply comprising at least one rechargeable battery.

8. The assembly according to claim 1, further comprising:
- each of said headphones having a front side, a back side and an outer side extending therebetween, said outer side having a plurality of intersecting sides such that each of said headphones has a triangular shape for accommodating ears of the canine, said front side being open into an interior of said headphones;
- a pair of cushions, each of said cushions being coupled to said front side of a respective one of said headphones wherein each of said cushions is configured to abut the canine's head when said headphones are worn on the canine's head, each of said cushions being positioned on said front side of said respective headphone, each of said cushions being coextensive with an intersection between said front side and said outer side of said respective headphone;
- a pair of membranes, each of said membranes being coupled to a respective one of said headphones, each of said membranes being comprised of a sound permeable material wherein each of said membranes is configured to pass sound therethrough, each of said membranes being positioned on said front side of said respective headphone such that each of said membranes covers said front side;
- each of said straps having a first end and a second end, said first end of each of said straps being coupled to a respective one of said intersecting sides of said outer side of a respective one of said headphones, said second end of each of said straps being coupled to a respective one of said intersecting sides of said outer side of a respective one of said headphones, each of said straps comprising a first portion slidably engaging a second portion such that each of said straps has an adjustable length; and
- a switch being slidably coupled to a respective one of said headphones, said switch being electrically coupled to said control circuit, said switch being positionable between an on position and an off position for turning said control circuit on and off; and
- a power supply being integrated into a respective one of said headphones, said power supply being electrically coupled to said control circuit, said power supply comprising at least one rechargeable battery.

* * * * *